(12) United States Patent
Dolitzky et al.

(10) Patent No.: US 7,820,816 B2
(45) Date of Patent: Oct. 26, 2010

(54) PROCESS FOR THE SYNTHESIS OF CMHTP AND INTERMEDIATES THEREOF

(75) Inventors: Ben-Zion Dolitzky, Petach Tiqva (IL); Evgeny Shapiro, Haifa (IL); Santiago Ini, Haifa (IL); Yaron Shmuely, Hedera (IL); Eli Lancry, Modiin (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 127 days.

(21) Appl. No.: 11/892,532

(22) Filed: Aug. 23, 2007

(65) Prior Publication Data

US 2008/0200676 A1 Aug. 21, 2008

Related U.S. Application Data

(60) Provisional application No. 60/839,428, filed on Aug. 23, 2006, provisional application No. 60/963,019, filed on Aug. 1, 2007, provisional application No. 60/928,745, filed on May 10, 2007, provisional application No. 60/935,093, filed on Jul. 26, 2007.

(51) Int. Cl.
*C07D 471/02* (2006.01)
(52) U.S. Cl. ..................................... 544/279
(58) Field of Classification Search .................. 544/282, 544/279
See application file for complete search history.

(56) References Cited

U.S. PATENT DOCUMENTS

| | | | |
|---|---|---|---|
| 5,158,952 A * | 10/1992 | Janssen et al. | 514/259.41 |
| 5,254,556 A | 10/1993 | Janssen et al. | |
| 5,688,799 A | 11/1997 | Vandenberk et al. | |
| 6,320,048 B1 | 11/2001 | Janssen et al. | |
| 6,325,826 B1 | 12/2001 | Vardi | |
| 2005/0060027 A1 | 3/2005 | Khenansho | |
| 2007/0150046 A1 | 6/2007 | Meyer et al. | |
| 2007/0260303 A1 | 11/2007 | Hegg | |
| 2008/0171875 A1 | 7/2008 | Ini et al. | |
| 2008/0171876 A1 | 7/2008 | Ini et al. | |
| 2008/0177067 A1 | 7/2008 | Dolitzky et al. | |
| 2008/0200676 A1 | 8/2008 | Dolitzky et al. | |
| 2008/0214808 A1 | 9/2008 | Spittaels et al. | |
| 2008/0214809 A1 | 9/2008 | Dolitzky et al. | |
| 2008/0281100 A1 | 11/2008 | Ini et al. | |

FOREIGN PATENT DOCUMENTS

| | | | |
|---|---|---|---|
| CN | 101245065 | | 8/2008 |
| EP | 368388 | * | 5/1990 |
| EP | 0 368 388 | | 7/1991 |
| EP | 0 730 594 | | 9/1999 |
| EP | 1 879 890 | | 1/2008 |
| WO | WO 95/14691 | | 6/1995 |
| WO | WO 96/23784 | | 8/1996 |
| WO | WO 0212200 | * | 2/2002 |
| WO | WO 0214286 | * | 2/2002 |
| WO | WO 2006/027370 | | 3/2006 |
| WO | WO 2006/114384 | | 11/2006 |
| WO | WO 2008/021342 | | 2/2008 |
| WO | WO 2008/021345 | | 2/2008 |
| WO | WO 2008/021346 | | 2/2008 |
| WO | WO 2008024415 | * | 2/2008 |
| WO | WO 2008/087557 | | 7/2008 |
| WO | WO 2008/108957 | | 9/2008 |
| WO | WO 2008/128436 | | 10/2008 |
| WO | WO 2008/140641 | | 11/2008 |
| WO | WO 2008/140646 | | 11/2008 |
| WO | WO 2008/144073 | | 11/2008 |

OTHER PUBLICATIONS

De Smet, at al., Org. Proc. Res. & Develop. (2005), 9(3), 344-347.*
International Search Report of PCT Int'l Application No. PCT/US2007/018594, dated Jan. 29, 2009.
De Smet, et al., "Selective Control by Use of Near-IR for a Hydrogenation Process" *Organic Process Research & Development*, vol. 9, No. 3 (2005), 344-347.
El-Sayed Badawey and Thomas Kappe "Synthesis of Some New Imidazo (1,2-A) Pyrimidin-5(1H)-Ones as Potential Antineoplastic Agents" *Journal of Heterocyclic Chemistry*, vol. 32, 1995, pp. 1003-1006.

* cited by examiner

*Primary Examiner*—James O Wilson
*Assistant Examiner*—Cecilia M Jaisle
(74) *Attorney, Agent, or Firm*—Kenyon & Kenyon LLP

(57) ABSTRACT

The present invention provides 3-benzyloxy-2-aminopyridine (BOPA), 3-(2-Hydroxyethyl)-2-methyl-9-hydoxy-4H-pyrido[1,2-a]pyrimidine-4-one (HMBP), 3-(2-Chloroethyl)-2-methyl-9-hydoxy-4H-pyrido[1,2-a]pyrimidine-4-one (CMHP) and 3-(2-chloroethyl)-6,7,8,9-tetrahydro-9-hydroxy-2-methyl-4H-pyrrido[1,2-a]-pyrimidin-4-one (CMHTP) useful as intermediates for the preparation of paliperidone. The present invention also provides processes for preparing these intermediates and for preparing paliperidone.

15 Claims, 2 Drawing Sheets

PROCESS FOR THE SYNTHESIS OF CMHTP AND INTERMEDIATES THEREOF

CROSS REFERENCE TO RELATED APPLICATIONS

This patent application claims the benefits of U.S. Provisional Application No. 60/839,428 filed Aug. 23, 2006, No. 60/963,019 filed on Aug. 1, 2007, No. 60/928,745 filed May 10, 2007 and No. 60/935,093 filed Jul. 26, 2007, the disclosures of which are hereby incorporated by reference.

FIELD OF THE INVENTION

The invention concerns a process for the synthesis of CMHTP, an intermediate in the synthesis of Paliperidone.

BACKGROUND OF THE INVENTION

Paliperidone, 3-[2-[4-(6-fluorobenzo[d]isoxazol-3-yl)-1-piperidyl]ethyl]-7-hydroxy-4-methyl-1,5-diazabicyclo[4.4.0]deca-3,5-dien-2-one, is a 5-HT antagonist belonging to the chemical class of benzisoxazole derivatives and a racemic mixture having the following structural formula:

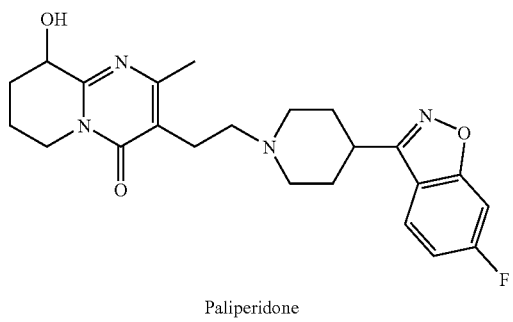

Paliperidone

Paliperidone is a metabolite of Risperidone. Marketed under the name, Invega®, Paliperidone is a psychotropic agent approved in the United States for the treatment of schizophrenia.

A process for the synthesis of Paliperidone, is described in U.S. Pat. No. 5,158,952 according to the following scheme.

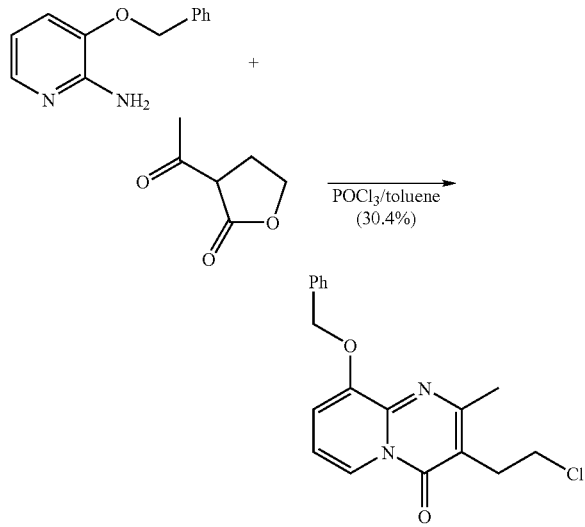

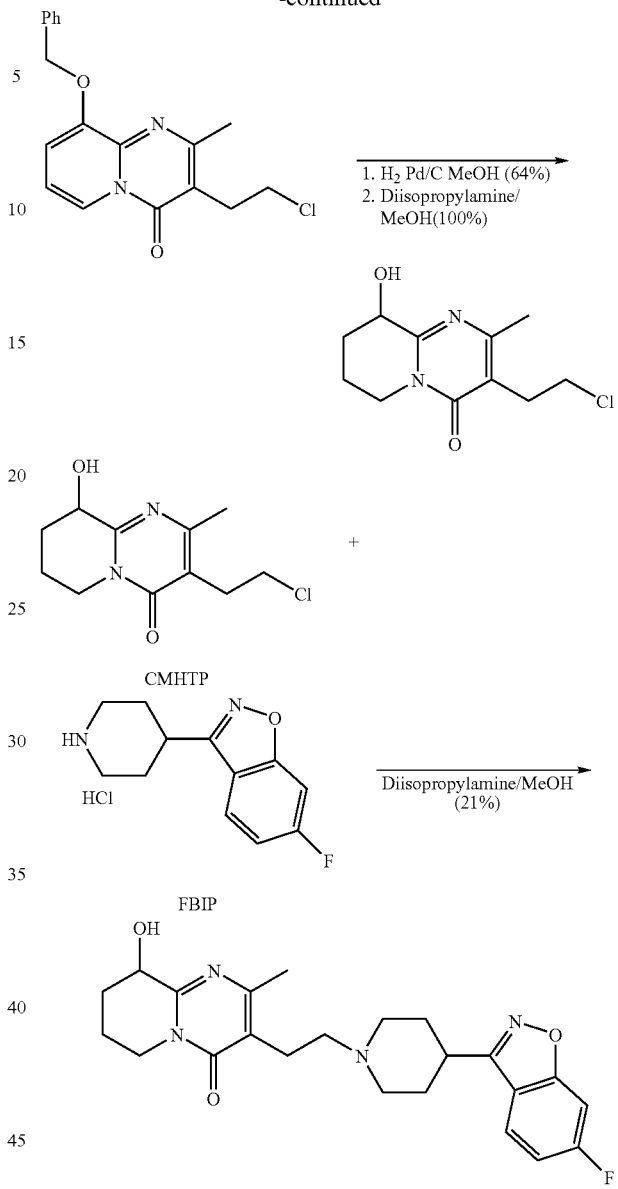

The preparation of paliperidone via the intermediate 3-(2-chloroethyl)-6,7,8,9-tetrahydro-9-hydroxy-2-methyl-4H-pyrrido[1,2-a]-pyrimidin-4-one (CMHTP) is depicted in the last step of the above scheme. This process is performed in the presence of an organic base.

Process for the synthesis of intermediates of Paliperidone is described also in U.S. Pat. No. 5,688,799.

The processes described in the above publications are long, and result in low chemical yields, making their application in the industry very hard. There is a need in the art for a new process for preparing Paliperidone and its intermediates.

SUMMARY OF THE INVENTION

One of the embodiments of the invention provides a process for preparing 3-(2-chloroethyl)-6,7,8,9-tetrahydro-9-hydroxy-2-methyl-4H-pyrrido[1,2-a]-pyrimidin-4-one (CMHTP), comprising:

(A) removing the benzyl group from 3-(2-chloroethyl)-2-methyl-9-benzyloxy-4H-pyrido[1,2-a]pyrimidine-4-one (CMBP) to form 3-(2-chloroethyl)-2-methyl-9-hydoxy-4H-pyrido[1,2-a]pyrimidine-4-one (CMHP);

(B) reacting the product of step (A) with hydrogen and a hydrogenation catalyst to form CMHTP; and (C) recovering or isolating the CMHTP.

Another embodiment of the invention provides a process for preparing CMHTP, comprising:

(a) mixing 3-(2-hydroxyethyl)-2-methyl-9-benzyloxy-4H-pyrido[1,2-a]pyrimidine-4-one (HMBP) and POCl₃ to form a reaction residue;

(b) combining the reaction residue with methanol and toluene to obtain a precipitate of 3-(2-chloroethyl)-2-methyl-9-hydoxy-4H-pyrido[1,2-a]pyrimidine-4-one (CMHP);

(c) reacting the product of step (b) with hydrogen and a hydrogenation catalyst to form CMHTP; and (d) recovering or isolating the CMHTP.

An embodiment of the invention provides a process for preparing 3-(2-chloroethyl)-2-methyl-9-hydoxy-4H-pyrido[1,2-a]pyrimidine-4-one (CMHP), comprising:

(a) mixing 3-(2-hydroxyethyl)-2-methyl-9-benzyloxy-4H-pyrido[1,2-a]pyrimidine-4-one (HMBP) and POCl₃ to form a reaction residue;

(b) combining the reaction residue with methanol and toluene to obtain a precipitate of CMHP; and (c) recovering or isolating the CMHP.

One of the embodiments of the invention provides a process for preparing 3-(2-chloroethyl)-2-methyl-9-benzyloxy-4H-pyrido[1,2-a]pyrimidine-4-one (CMBP), comprising:

(I) mixing 3-(2-hydroxyethyl)-6,7,8,9-tetrahydro-9-benzyloxy-2-methyl-4H-pyrrido[1,2-a]-pyrimidin-4-one (HMBP) and POCl₃ to form a mixture;

(II) heating the mixture from step (I) to obtain a reaction residue;

(III) combining the reaction residue with ammonium hydroxide to obtain a two phase system; and (IV) recovering or isolating 3-(2-chloroethyl)-2-methyl-9-benzyloxy-4H-pyrido[1,2-a]pyrimidine-4-one (CMBP) from the organic phase of the two phase system of step (III).

The present invention also provides a process for preparing 3-(2-chloroethyl)-2-methyl-9-benzyloxy-4H-pyrido[1,2-a]pyrimidine-4-one (CMBP), comprising:

(A) mixing 3-benzyloxy-2-aminopyridine (BOPA), 3-acetyl-4,5-dihydro-3H-2-furanone (ADHF), at least one water absorbent and at least one aromatic solvent to form a mixture;

(B) heating the mixture formed in step (A) to obtain 3-(2-hydroxyethyl)-6,7,8,9-tetrahydro-9-benzyloxy-2-methyl-4H-pyrrido[1,2-a]-pyrimidin-4-one (HMBP);

(C) recovering or isolating the HMBP; and (D) reacting the HMBP with a chlorinating agent to form the CMBP.

The present invention also provides a process for preparing 3-(2-hydroxyethyl)-6,7,8,9-tetrahydro-9-benzyloxy-2-methyl-4H-pyrrido [1,2-a]-pyrimidin-4-one (HMBP), comprising:

(A) mixing 3-benzyloxy-2-aminopyridine (BOPA), 3-acetyl-4,5-dihydro-3H-2-furanone (ADHF), at least one water absorbent and at least one aromatic solvent to form a mixture;

(B) heating the mixture formed in step (A) to obtain 3-(2-hydroxyethyl)-6,7,8,9-tetrahydro-9-benzyloxy-2-methyl-4H-pyrrido[1,2-a]-pyrimidin-4-one (HMBP); and (C) recovering or isolating the HMBP.

One of the embodiments of the invention provides a process for preparing 3-benzyloxy-2-aminopyridine (BOPA), comprising:

alkylating 2-amino-3-hydroxypyridine (HAP) with benzyl bromide in the presence of a base to form 3-benzyloxy-2-aminopyridine (BOPA); and recovering or isolating the BOPA.

In some of the embodiments of the present invention, two or more of the above processes of the invention are combined sequentially.

The present invention also provides processes for preparing paliperidone by converting recovered or substantially isolated CMHTP prepared by any of the processes for preparing CMHTP of the invention into paliperidone. These processes may be combined with other processes of the invention for preparing one or more of the intermediates.

The present invention also provides processes for preparing paliperidone by converting CMHTP into paliperidone, wherein the conversion is preceded, albeit not immediately, by a step using recovered or substantially isolated HMBP. These processes may be combined with other processes of the invention for preparing the HMBP or another intermediate preceding the formation of HMBP.

The present invention also provides processes for preparing paliperidone by converting CMHTP into paliperidone, wherein the conversion is preceded, albeit not immediately, by a step reacting HAP with benzyl bromide to prepare BOPA as one of the intermediates.

The present invention also provides processes for preparing paliperidone by combining two or more processes of the present invention in an appropriate sequential order.

One of the embodiments of the invention provides a process for preparing paliperidone, comprising:

(A) removing the benzyl group from 3-(2-chloroethyl)-2-methyl-9-benzyloxy-4H-pyrido[1,2-a]pyrimidine-4-one (CMBP) to form 3-(2-chloroethyl)-2-methyl-9-hydoxy-4H-pyrido[1,2-a]pyrimidine-4-one (CMHP);

(B) reacting the product of step (A) with hydrogen and a hydrogenation catalyst to form 3-(2-chloroethyl)-6,7,8,9-tetrahydro-9-hydroxy-2-methyl-4H-pyrrido[1,2-a]-pyrimidin-4-one (CMHTP);

(C) recovering or isolating the CMHTP; and (D) condensing the recovered or isolated CMHTP with 6-fluoro-3-piperidino-1,2-benisoxazol (FPBI) to form paliperidone.

In an embodiment, the present invention provides a process for preparing paliperidone, comprising:

(a) mixing 3-(2-hydroxyethyl)-2-methyl-9-benzyloxy-4H-pyrido[1,2-a]pyrimidine-4-one (HMBP) and POCl₃ to form a reaction residue;

(b) combining the reaction residue with methanol and toluene to obtain a precipitate of 3-(2-chloroethyl)-2-methyl-9-hydoxy-4H-pyrido[1,2-a]pyrimidine-4-one (CMHP);

(c) reacting the product of step (b) with hydrogen and a hydrogenation catalyst to form 3-(2-chloroethyl)-6,7,8,9-tetrahydro-9-hydroxy-2-methyl-4H-pyrrido[1,2-a]-pyrimidin-4-one (CMHTP);

(d) recovering or isolating the CMHTP; and (e) condensing the recovered or isolated CMHTP with 6-fluoro-3-piperidino-1,2-benisoxazol (FPBI) to form paliperidone.

In an embodiment, the present invention provides a process of preparing pallperidone, comprising:

condensing recovered or substantially isolated 3-(2-chloroethyl)-6,7,8,9-tetrahydro-9-hydroxy-2-methyl-4H-pyrrido[1,2-a]-pyrimidin-4-one (CMHTP) with 6-fluoro-3-piperidino-1,2-benisoxazol (FPBI) to form paliperidone.

The present invention also provides recovered or substantially isolated CMHTP, and processes of using the recovered or substantially isolated CMHTP to form paliperidone.

The present invention also provides crystalline 3-(2-chloroethyl)-6,7,8,9-tetrahydro-9-hydroxy-2-methyl-4H-pyrrido[1,2-a]-pyrimidin-4-one (CMHTP) characterized by powder X-ray diffraction (PXRD) peaks at about 9.7, 19.4, 22.9 and 24.9+/−0.2 degrees 2θ.

The present invention also provides crystalline 3-(2-chloroethyl)-6,7,8,9-tetrahydro-9-hydroxy-2-methyl-4H-pyrrido[1,2-a]-pyrimidin-4-one (CMHTP) characterized by powder X-ray diffraction (PXRD) peaks at about 8.5, 11.2, 15.3, 23.8+/−0.2 degrees 2θ.

In an embodiment, the present invention provides a process for preparing crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 9.7, 19.4, 22.9 and 24.9+/−0.2 degrees 2θ, comprising crystallizing CMHTP from ethyl acetate.

In an embodiment, the present invention provides a process for preparing crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 8.5, 11.2, 15.3, 23.8+/−0.2 degrees 2θ, comprising:

stirring starting solid CMHTP in water to form the product CMHTP characterized by powder X-ray diffraction (PXRD) peaks at about 8.5, 11.2, 15.3, 23.8+/−0.2 degrees 2θ, wherein the starting solid CMHTP is crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 9.7, 19.4, 22.9 and 24.9+/−0.2 degrees 2θ.

Optionally, in the above process, after the starting solid CMHTP is stirred in water, a solid is obtained by filtration as the crystalline CMHTP characterized by powder X-ray diffraction (PXRD) peaks at about 9.7, 19.4, 22.9 and 24.9+/−0.2 degrees 2θ. The solid obtained by filtration is further optionally washed with water, then washed with ethyl acetate and dried.

In an embodiment, the present invention provides 3-(2-chloroethyl)-2-methyl-9-hydoxy-4H-pyrido[1,2-a]pyrimidine-4-one (CMHP).

The present invention also provides recovered or substantially isolated CMHP.

In an embodiment, the present invention provides 3-(2-hydroxyethyl)-2-methyl-9-benzyloxy-4H-pyrido[1,2-a]pyrimidine-4-one (HMBP).

In an embodiment, the present invention provides recovered or substantially isolated HMBP.

DETAILED DESCRIPTION OF THE INVENTION

Figure 1:
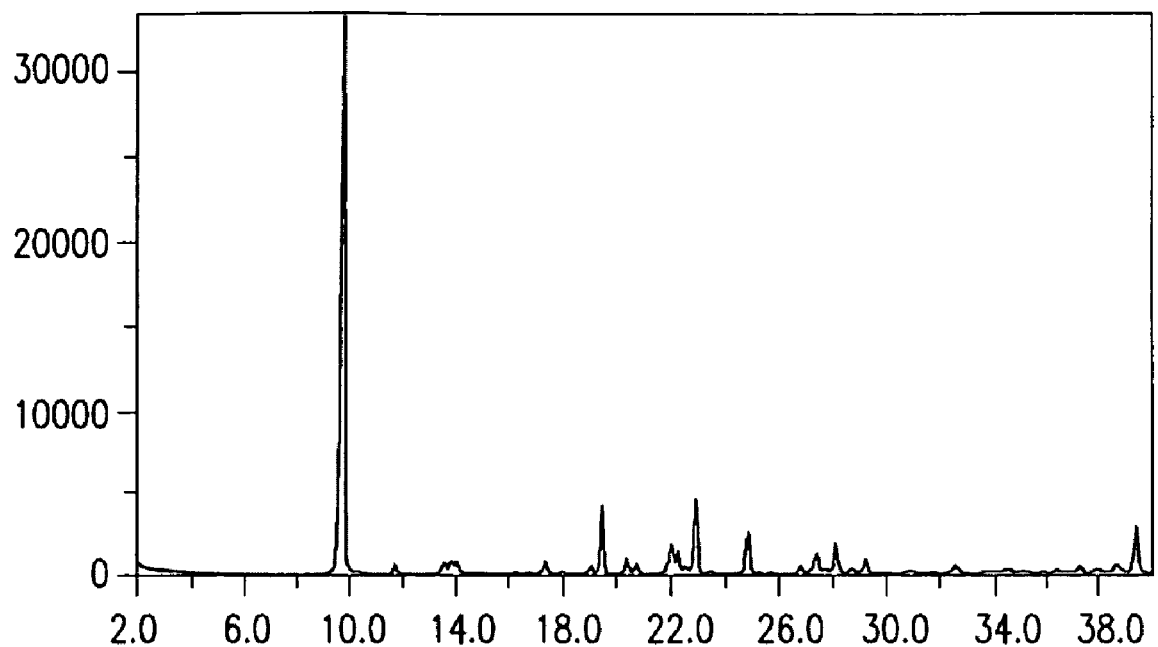
FIG. 1 illustrates a representative powder X-ray diffraction (PXRD) pattern for CMHTP Form I.

The present invention is based on a new synthetic route for obtaining 9-hydroxy risperidone (Paliperidone).

In one embodiment, the present invention provides a process for preparing 3-benzyloxy-2-aminopyridine (BOPA) using a benzyl bromide derivative.

In one example, the present invention provides a process for preparing 3-benzyloxy-2-aminopyridine (BOPA) via base-promoted alkylation of 2-amino-3-hydroxypyridine (HAP) with benzyl bromide.

For instance, this benzylation process can be conducted as described in the following scheme:

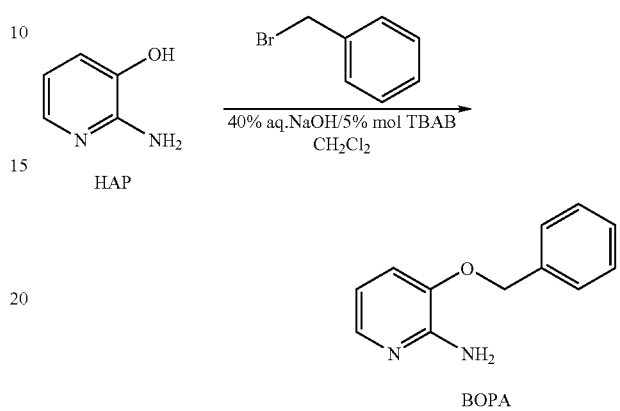

The starting material, HAP, is commercially available.

In one embodiment of the present invention of the process for preparing BOPA of the present invention, a mixture of HAP, benzyl bromide, sodium hydroxide, water, dichloromethane and tetrabutylammonium bromide is provided, then maintained at a temperature of about 20° C. for about 12 hours to obtain a two phase system. The temperature and time will be dependant on many factors such as the choice of base used, the amount of starting material and the yield desired. The BOPA can them be recovered from the organic phase by any means known in the art.

Preferably, HAP is first combined with a solution of sodium hydroxide, water and dichloromethane, and then tetrabutylammonium bromide is combined with the reaction mixture. Preferably, before combining with benzyl bromide, the reaction mixture is maintained for about 15 minutes. BOPA may be recovered from the organic phase by any method known in the art.

The present invention also provides a process for preparing 3-(2-chloroethyl)-2-methyl-9-benzyloxy-4H-pyrido[1,2-a]pyrimidine-4-one (CMBP) by condensation of BOPA with 3-acetyl-4,5-dihydro-3H-2-furanone (ADHF) to produce 3-(2-hydroxyethyl)-6,7,8,9-tetrahydro-9-benzyloxy-2-methyl-4H-pyrrido[1,2-a]-pyrimidin-4-one (HMBP) and further chlorinating HMBP to produce CMBP. For instance, the process can be conducted as described in the following scheme.

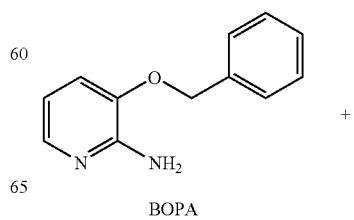

BOPA

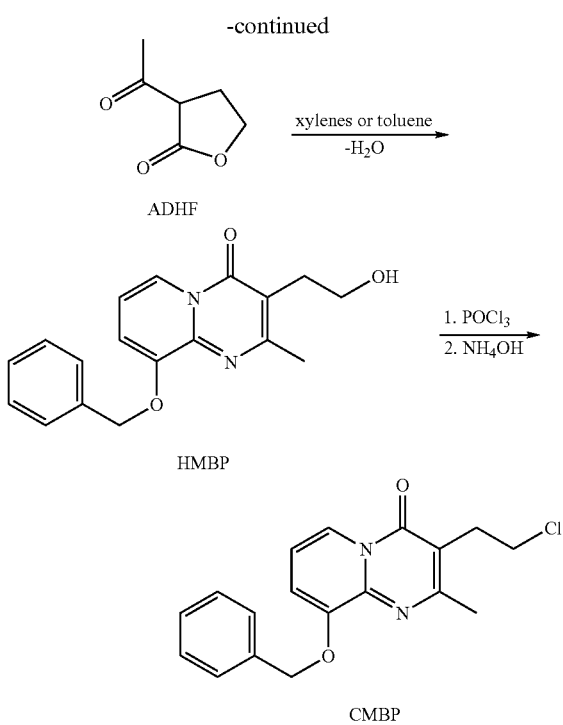

In one embodiment of the present invention, a process is presented for preparing CMBP from BOPA and ADHF wherein the HMBP is recovered. In the process for this aspect of the invention, BOPA and ADHF are reacted to obtain HMBP, which is then recovered and optionally subsequently converted into CMBP. According to the process of this invention, the HMBP may be produces according to any method known in the art but is then recovered and preferably isolated. For example, HMBP may be prepared by a process comprising: providing a mixture of BOPA, ADHF and one or more water absorbents such as p-toluenesulfonic acid (TsOH), $H_2SO_4$ or a water separator such as a Dean Stark water extraction system as well as one or more aromatic solvents such as xylene or toluene; heating to reflux to obtain crude HMBP. Preferably, the mixture is maintained at room temperature to reflux for about 12 hours to about 30 hours, although the time and temperature necessary are dependant on a number of factors including materials chosen and quantity. Preferably, while bringing the mixture to reflux, water is removed. More preferably, the water removal is done by using a water separator. Preferably, the crude HMBP is further crystallized from one or more polar, aprotic organic solvents such as methyl ether ketone, acetone, nitromethane, acetonitrile, N-methylpyrrolidone, dimethyl formamide or DMSO and preferably acetonitrile.

Recovery may be by crystallization. Crystallization may be caused by reducing the volume of the solvents and/or by cooling. In one example, the solvents present with the crude HMBP is reduced to induce crystallization. Subsequently, the HMBP may be recrystallized. Specifically, useful solvents in the crystallization process include:organic solvent for example: methyl ether ketone, acetone, nitromethane, acetonitrile, N-methylpyrrolidone, dimethyl formamide or DMSO and preferably acetonitrile.

In another embodiment of the present invention, the HMBP is solid or isolated.

In another embodiment of the present invention, the HMBP is substantially pure. Purity may be at least 50% chemically pure, preferably at least 70% chemically pure, more preferably at least 90% chemically pure and most preferably at least 95% chemically pure.

Once recovered, the HMBP can then be converted into CMBP. In one embodiment, the HMBP is converted by a process comprising: providing a second mixture of HMBP and $POCl_3$; heating the mixture to obtain a reaction residue; combining the reaction residue with ammonium hydroxide to obtain a two phase system having an aqueous and an organic phase, and recovering crude CMBP from the organic phase. Preferably, the mixture is heated to a temperature of greater than 90° C. Preferably, the $POCl_3$ used is distilled. Preferably, prior to combining with ammonium hydroxide, the reaction residue is cooled. Preferably, the crude CMBP is further extracted with toluene. More preferably, extractions are performed with toluene at a temperature of about 90° C.

In another embodiment of the present invention solid 3-(2-chloroethyl)-6,7,8,9-tetrahydro-9-hydroxy-2-methyl-4H-pyrrido[1,2-a]-pyrimidin-4-one (herein referred to as "CMHTP") in crystalline or amorpous form is presented. This solid CMHTP can be in crystalline form. In one example, crystalline CMHTP Form I is presented characterized as having PXRD peaks at about 9.7, 19.4, 22.9 and 24.9+/−0.2 degrees 2θ. Additional PXRD peaks may additionally be present at one or more of the following positions: about 22.0, 27.4, 28.1 and 39.4+/−0.2 degrees 2θ. The PXRD pattern of CMHTP Form I can be substantially as the PXRD shown in FIG. 1.

In another embodiment of the invention, the CMHTP Form I has a polymorphic purity of at least about 50%, preferably at least about 90%, more preferably at least about 95% and most preferably at least about 99%.

In another embodiment of the invention, solid CMHTP Form II is presented, having characteristic PXRD peaks at about: 8.5, 11.2, 15.3, 23.8+/−0.2 two theta. Preferably, the characteristic PXRD pattern of CMHTP Form II also includes one or more additional peaks of the following: about 17.0, 22.6, 25.6 and 29.7+/−0.2 degrees 2θ. The PXRD pattern of CMHTP form II can be substantially as the PXRD pattern shown in FIG. 2.

In another embodiment of the invention, the CMHTP Form II has a polymorphic purity of at least about 50%, preferably at least about 90%, and more preferably at least about 95% and most preferably at least about 99%.

The powder X-ray diffraction patterns disclosed in this patent application were collected using an X-ray diffractometer with Cu radiation at λ=1.5418 Å.

In another embodiment of the present invention, the CMHTP described above is converted into paliperidone.

In another embodiment, the present invention provides a process for preparing 3-(2-chloroethyl)-6,7,8,9-tetrahydro-9-hydroxy-2-methyl-4H-pyrrido[1,2-a]-pyrimidin-4-one (CMHTP) from CMBP comprising via hydrogenation using hydrogen, preferably hyperbaric hydrogen, more preferably hydrogen at about 1.5 bar to about 3.5 bar, most preferably hydrogen at 2.5 bar to 3.0 bar, with a catalyst selected from the group of: Pd/C/338, Pd/C/871, Pd/C/490, Raney-Nickel, platinum oxide, rhodium on carbon and platinum on carbon to form CMHTP, followed by recovery or isolation of the CMHTP formed.

In another embodiment, the present invention provides a process for preparing 3-(2-chloroethyl)-6,7,8,9-tetrahydro-9-hydroxy-2-methyl-4H-pyrrido[1,2-a]-pyrimidin-4-one (CMHTP) from CMBP comprising removing the benzyl protection from CMBP to produce 3-(2-chloroethyl)-2-methyl- 9-hydroxy-4H-pyrido[1,2-a]pyrimidine-4-one (CMHP) and further hydrogenating the condensed pyridine ring in the CMHP using hydrogen with a hydrogenation catalyst to form CMHTP and then recovering the CMHTP. The hydrogenation catalyst can be selected from the group of: Pd/C/338, Pd/C/871, Pd/C/490, Raney-Nickel, platinum oxide, rhodium on carbon and platinum on carbon. The hydrogen used is preferably hyperbaric hydrogen, more preferably hydrogen at about 1.5 bar to about 3.5 bar, most preferably hydrogen at 2.5 bar to 3.0 bar Alternatively, the CMHP may be produced by removing the benzyl protection from HMBP during the chlorination. For instance, the process for preparing CMHTP can be conducted as described in the following scheme:

Treating the mixture with HCl results in lower amounts of the impurities 3-vinyl-6,7,8,9-tetrahydro-9-hydroxy-2-methyl-4H-pyrrido[1,2-a]-pyrimidin-4-one (MHDP) and 3-ethyl-6,7,8,9-tetrahydro-9-hydroxy-2-methyl-4H-pyrrido [1,2-a]-pyrimidin-4-one (MHTP).

In another embodiment, the present invention provides CMHTP with less than 10%, preferably less than 5%, more preferably less than 4% and most preferably less than 0.5% of MHDP based on area percent as measured by HPLC. The present invention also provides substantially pure CMHTP having less than 17%, preferably less than 13%, more preferably less than 6% and most preferably less than 5% of MHTP as measured by area percent of HPLC.

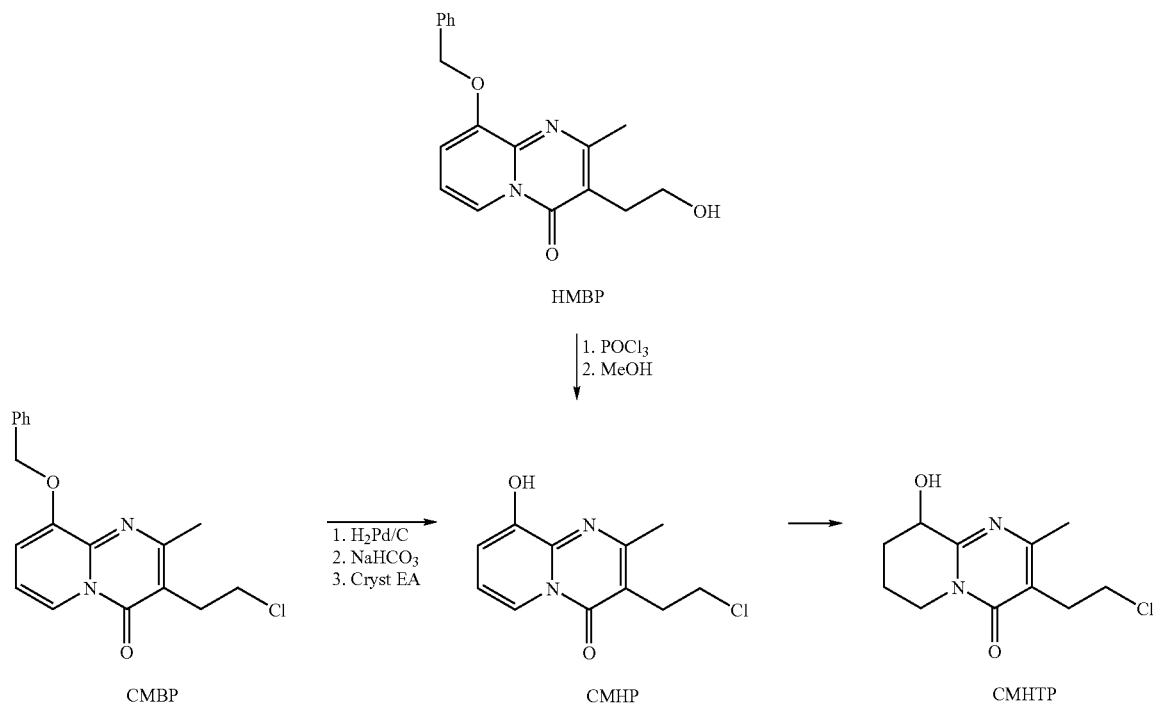

In one embodiment, the present invention provides 3-(2-chloroethyl)-2-methyl-9-hydroxy-4H-pyrido[1,2-a]pyrimidine-4-one (CMHP).

In another embodiment of the present invention a process is provided for preparing CMHTP comprising: providing a mixture of CMBP, HCl and a catalyst such as palladium on charcoal in a solvent such as methanol; treating with hydrogen; and removal of the solvent to obtain CMHTP.

Preferably, the HCl is combined with a solution of CMBP and methanol, and the mixture is then combined with the catalyst. The catalyst can be any hydrogenation catalyst known to a skilled artisan including: 10% Pd/C/338, 10% Pd/C/87L, 10% Pd/C/490, Ra—Ni5, 5% Rh/C/592, PtO, 5% Pt/C/117. Most preferably, the catalyst is 10% Pd/C./338.

Preferably, after treating with hydrogen, the mixture is heated to a temperature of about 65° C. Preferably, prior to the removal of the solvent the mixture is cooled to about 20° C. Preferably, the solvent is removed by evaporation, more preferably, under reduced pressure.

The process may further comprise neutralizing the obtained CMHTP HCl salt, with an inorganic base, e.g., $KHCO_3$ or, preferably, $NaHCO_3$. CMHTP may then be recovered by any method known in the art.

In the process of the invention, the intermediate CMHP can also be obtained directly form HMBP.

In one of the embodiments of the present invention the process for preparing CMHP comprises reacting a mixture of HMBP and $POCl_3$ to form a reaction residue; combining the reaction residue with a solution of methanol and toluene to obtain a precipitate of crude CMHP, and recovering the crude CMHP. Preferably, the mixture of HMBP and $POCl_3$ is heated to obtain the reaction residue. More preferably, the mixture of HMBP and $POCl_3$ is heated to about 70° C. to about reflux.

Preferably, while combining with a solution of methanol and toluene, the reaction residue is maintained at a temperature of about 60° C.

Preferably, the crude CMHP is recovered by any method known to the skilled in the art. Such methods include, but are not limited to, washing with toluene and further drying the obtained CMHP.

In another embodiment, the present invention provides a process for preparing paliperidone by coupling CMHTP with 6-fluoro-3-piperidino-1,2-benisoxazol (FPBI). For instance, the process for preparing paliperidone can be conducted as described in the following scheme:

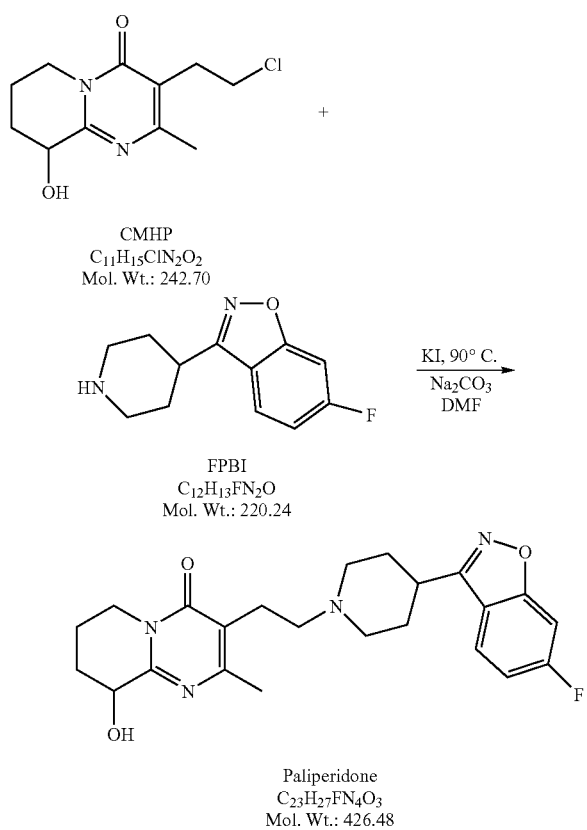

CMHP
C₁₁H₁₅ClN₂O₂
Mol. Wt.: 242.70

FPBI
C₁₂H₁₃FN₂O
Mol. Wt.: 220.24

KI, 90° C.
Na₂CO₃
DMF

Paliperidone
C₂₃H₂₇FN₄O₃
Mol. Wt.: 426.48

In another embodiment of the present invention, the CMHTP is subsequently used to prepare paliperidone. Although the general process for conversion of CMHTP to paliperidone is known in the art, the present invention provides a novel method of converting CMHTP to paliperidone using a recovered or isolated form of CMHTP (e.g., solid such as amorphous or, preferably, crystalline form of CMHTP) as the starting material which differs from the oily or liquid CMHTP residue used as the starting material without isolation in prior art processes for the preparation of paliperidone. In some of the embodiments of the process of the present invention for converting CMHTP to paliperidone, the liquid or oily CMHTP residue used as the starting material in prior art processes is replaced with an isolated form of CMHTP (e.g., solid such as amorphous or preferably crystalline, form of CMHTP) as the starting material. The present invention provides an embodiment of a process for converting CMHTP to paliperidone, wherein a mixture of CMHTP which is isolated, e.g., in a solid such as amorphous or preferably crystalline form, FPBI, sodium carbonate, potassium iodide and dimethylformamide (DMF) is heated to a temperature of about 90° C., then combined with water and extracted with dichloromethane (DCM) to obtain crude paliperidone.

Both CMHTP and FPBI starting materials can be in the form of a base or hydrogen halide salts. The FPBI starting material is commercially available. Preferably, the crude paliperidone is purified, for example, by recrystallization such as recrystallization from acetonitrile.

In an embodiment, the present invention provides recovered or substantially isolated CMHTP, e.g., in a solid form such as amorphous or preferably crystalline form.

The present invention provides processes for the preparation of paliperidone by converting substantially isolated or solid CMHTP to paliperidone.

In an embodiment, the present invention also provides recovered or substantially isolated HMBP in a solid form such as amorphous or preferably crystalline form.

The present invention provides processes for the preparation of paliperidone by using substantially isolated or solid HMBP as an intermediate.

In the processes disclosed herein for the preparation of paliperidone in the present invention, the processes can use substantially isolated or solid HMBP and substantially isolated or solid CMHTP as intermediates in different steps of the processes.

The present invention also provides sequential combination of a number of the reaction steps disclosed herein.

For instance, the present invention includes a process for preparing CMBP, comprising performing the process for preparing BOPA described above followed by performing the process for preparing CMBP described above using the BOPA prepared.

For instance, the present invention includes a process for preparing CMHTP, comprising performing the process for preparing BOPA described above, followed by performing the process for preparing CMBP described above, and followed by converting the CMBP to CMHTP according to the process described above.

For instance, the present invention includes a process for preparing 9-hydroxy risperidone, comprising performing the process for preparing BOPA described above, followed by performing the process for preparing CMBP described above, followed by converting the CMBP to CMHTP according to the process described above, and followed by performing the process for preparing 9-hydroxy risperidone using the CMHTP according to the process described above.

For instance, the present invention includes a process for preparing paliperidone, comprising performing a process for preparing CMHTP as described above, followed by performing the process for preparing paliperidone using the CMHTP according to the process described above, wherein the process for preparing CMHTP can start with CMHTP.HCl or CMBP.

For instance, the present invention includes a process for preparing paliperidone, comprising performing a process for preparing CMBP as described above, followed by converting the CMBP to CMHTP according to the process described above, and followed by performing the process for preparing paliperidone using the CMHTP according to the process described above, wherein the process for preparing the CMBP can start with HMBP or BOPA.

For instance, the present invention includes a process for preparing CMHTP, comprising performing the process for preparing CMBP described above, followed by converting the CMBP to CMHTP according to the process described above, wherein the preparation of CMBP can start with HMBP or BOPA.

Having described the invention with reference to certain preferred embodiments, other embodiments will become apparent to one skilled in the art from consideration of the specification. The invention is further defined by reference to the following examples describing in detail the synthesis of 9-hydroxy risperidone. It will be apparent to those skilled in the art that many modifications, both to materials and methods, may be practiced without departing from the scope of the invention.

EXAMPLES

Preparation of 3-benzyloxy-2-aminopyridine (BOPA)

Example 1

NaOH (40.04 g, 1 mol) was dissolved in water (60 ml) and covered with DCM (100 ml). AHP (20.04 g, 0.178 mol) was added to the reaction mixture in portions, under stirring, followed by the catalyst, TBAB (1.05 g). The reaction mixture was stirred for 15 min at 25-30° C. and treated with a solution of benzyl bromide (33.90 g, 0.194 mol) in DCM (80 ml). The reaction mixture was stirred overnight at 20° C. and diluted with water (100 ml). The organic phase was separated, and the aqueous phase was extracted with DCM (100 ml). The organic extracts were combined, washed with water (3×100 ml), then washed with brine (100 ml), dried with anhydrous magnesium sulfate, filtered, and evaporated under reduced pressure to afford 37.8 g of the title product in a purity of 93% (GC), as a solid. Yield 98%.

Preparation of 3-(2-hydroxyethyl)-6,7,8,9-tetrahydro-9-benzyloxy-2-methyl-4H-pyrrido[1,2-a]-pyrimidin-4-one (HMBP)

Example 2

A mixture of BOPA (28.22 g, 0.131 mol), ADHF (34.3 g, 0.262 mol) and TsOH (2.29 g) in xylene (150 ml) was brought to reflux and stirred overnight, using a water separator (Dean-Stark). Volatiles were removed under reduced pressure to afford 59.65 g of the crude product, which was crystallized from acetonitrile (250 ml). The colored crystals were filtered off, sucked on the sinter and dried in air, to afford 17.53 g of the title product, HMBP, as colored crystals. An additional amount of the title product (4.11 g) was isolated from the filtrate by a repeated crystallization. Total yield 53%, purity 92% (GC).

Example 3

A mixture of 3-benzyloxy-2-aminopyridine (BOPA) (1000.5 g), 3-acetyl-4,5-dihydro-2(3H)-furanone (ADHF) (965.0 g), p-toluenesulfonic acid, monohydrate (50.65 g), and toluene (1600 ml) was brought to reflux and stirred for 30 h, using a water separator (Dean-Stark) to collect ~83 g of water, until the level of BOPA was reduced to 3%.

The solution was cooled for 1.5 h to 65° C., until the crystallization started. The mixture was aged for 0.6 h, cooled to 5° C., and aged overnight, under stirring, to complete the crystallization. The crystalline mass was filtered. The cake was washed with cold toluene (~500 ml) to afford 1631 g of wet product, HMBP, as a pale solid. Purity 95% (HPLC area %), wetness 10%, yield 90%.

The wet product was directly used in the next stage (see Example 4). The mother liquor was evaporated to remove toluene and the residue was distilled under reduced pressure to afford 312 g of 3-acetyl-4,5-dihydro-2(3H)-furanone (ADHF) with a purity of 99%, which could be used for more synthesis of HMBP. Yield of the recovery was 96%.

Preparation of 3-(2-chloroethyl)-2-methyl-9-benzyloxy-4H-pyrido[1,2-a]pyrimidine-4-one (CMBP)

Example 4

Without Solvent

A mixture of HMBP (15.07 g, 0.0461 mol) and freshly distilled $POCl_3$ was heated under reflux for 5.5 h, in a 120° C. bath, under stirring, protected by a $CaCl_2$-tube. The excess $POCl_3$ was removed under reduced pressure and the reaction residue was treated with crushed ice (~100 g) and water (75 g), followed by a 24% ammonium hydroxide solution (90 ml). The organic phase was separated, the aqueous phase was extracted with DCM (3×200 ml), and discarded. The organic extracts were combined, washed with water (4×200 ml), dried with anhydrous magnesium sulfate, filtered, and evaporated under reduced pressure to afford 14.4 g crude product as a solidifying oil. The residue was extracted with hot toluene (90° C., 150 and 50 ml). The toluene extracts were combined and concentrated to ½-volume, to cause crystallization. The residue was filtered off, washed with cold toluene and dried at 45° C. under reduced pressure to afford 7.34 g of the title product, as a pink solid. Additional amounts of the title product (1.92 and 1.0 g) were isolated from the filtrate by repeat crystallization. Total yield 68%, purity 94%.

Example 5

Diglyme (bis(2-methoxyethyl) ether) (420 ml), wet 3-(2-hydroxyethyl)-2-methyl-9-benzyloxy-4H-pyrido[1,2-a]-pyrimidine-4-one (HMBP, 351.2 g, assay 90%), and $POCl_3$ (351.5 g) were charged into a reactor, under inert atmosphere. The reaction suspension was heated to 90° C., under stirring, to afford a clear solution. The solution was stirred for 4.5 h at 90-92° C. until the level of HMBP reduced to <0.5%.

The reaction mixture was diluted with toluene (850 ml) allowing the mixture to cool to 40-50° C. Water (800 ml) was carefully fed to the reaction mixture for 15 min, maintaining the temperature below 71° C.

The mixture was stirred allowing the temperature to decrease to 64° C. A 25% $NH_4OH$ (550 ml) was gradually fed to the reaction mixture for 10 min to adjust pH 7, maintaining the temperature below 80° C.

The stirrer was stopped to afford two clear phases. The lower aqueous phase (1539 g, colored liquid, pH 7) was separated and discarded. The hot organic phase was washed twice with hot (~50° C.) water (205 and 200 ml) at 65-70° C. Lower aqueous phases (205.3 g and 216 g, respectively) were separated and discarded. The mixture was cooled to 5° C. for 1.7 h. The crystallization started at 46° C. The crystalline mixture was aged overnight at 5° C. and filtered. The cake was washed with cold toluene (50 ml) to afford 371.0 g of the wet crystalline product. The wet product was dried for 2 h at 75-80° C. to afford 289 g of the dry CMBP, as lilac powder. Purity 99.8% (HPLC). Yield 85%.

The mother liquor was evaporated to remove toluene. The filtrate was evaporated to afford 302.1 g of a viscous liquid which was cooled to 5° C. and stored overnight. The second crop (13.87 g) was collected and dried for 2 h at 70° C. to afford 13.39 g of CMBP, which could be used for more synthesis of CMBP. Purity 98%. Overall recovery yield was 89%.

Example 6

A mixture of 3-(2-hydroxyethyl)-2-methyl-9-benzyloxy-4H-pyrido[1,2-a]-pyrimidine-4-one (HMBP, 60.25 g) and $POCl_3$ (87.29 g) was charged into a 0.5 L reactor. The reaction mixture was brought to reflux (~100-105° C.) and stirred for 1.5 h, until the level of the substrate reduced to <0.5%. The remaining $POCl_3$ (33.11 g) was distilled off and the hot residue was dissolved with N,N-dimethylformamide [DMF] (84 ml) at 100° C. The clear solution was cooled to 0° C., under stirring, and quenched with ice water (150 ml), maintaining temperature below 50° C. The mixture was treated with cold (~0° C.) 25% $NH_4OH$ (150 ml), keeping the temperature below 40° C. The resulting suspension was stirred for 2 h at 40-45° C. and filtered. The cake was washed with water (100 g) to afford 59.0 g of wet crude product (wetness 26%. Assay 83% (calibrated HPLC), purity 94%, yield 63%.

The product was crystallized from toluene (270 ml) to afford 42.32 g of the wet product, which was dried for 4 h at 70° C. to afford 34.25 g of the crystalline CMBP. Purity 99.8%. Overall yield 56%.

Preparation of 3-(2-chloroethyl)-2-methyl-9-hydroxy-4H-pyrido[1,2-a]pyrimidine-4-one (CMHP)

Example 7

To a solution of 3-(2-hydroxyethyl)-2-methyl-9-hydroxy-4H-pyrido[1,2-a]pyrimidine-4-one (45.08 g) in N,N-dimethylformamide (DMF) (68 ml) $POCl_3$ (72.92 g) was fed, maintaining the temperature below 100° C. The resulting viscous liquid was aged for 2 h and cooled to 30° C., under stirring The water (~20 ml) was fed for 1 min to the cold reaction mixture to afford the precipitation. The temperature rose to 105° C. to afford clear solution. The feeding was stopped to allow the mixture to cool to 65° C. The remaining water (100 ml, total 120 ml) was added for 3 min, followed by a 25% $NH_4OH$ (134 ml) to adjust pH 7. New precipitation occurred. The mixture was cooled for 0.5 h to 10° C. and aged for 1 h, under stirring, to complete the precipitation. The crystalline mass was filtered and the cake was washed with water (2×100 ml) to afford 55.38 g of the wet product which was dried overnight at 75-80° C. to afford 30.5 g of dry CMHP. Yield 71%.

Example 8

Diglyme (80 ml), 3-(2-hydroxyethyl)-2-methyl-9-hydroxy-4H-pyrido[1,2-a]-pyrimidine-4-one (50.74 g), and $POCl_3$ (75.35 g) were charged into reactor. The reaction mixture was heated to 80-82° C., under stirring. The mixture was converted at 60° C. to a heavy paste which was finally transformed into a clear viscous liquid. The mixture was stirred for 4 h at 80-82° C. and cooled to 30° C. The mixture was carefully quenched with water (120 ml), maintaining the temperature below 85° C. Precipitation occurred. The reaction suspension was treated with a 25% $NH_4OH$ (115 ml) for 20 min to adjust pH 7, maintaining the temperature below 65° C. (cooling agent 30° C.). The mixture was cooled to room temperature (20-25° C.), under stirring, and aged for 1 h to complete the precipitation. The crystalline mass was filtered and the cake was washed with water (2×100 ml) to afford 51.70 g of the wet product, which was dried overnight at 75-80° C., under reduced pressure to afford 29.0 g of the dry CMHP. Yield 62%.

Example 9

Mixture of 3-(2-hydroxyethyl)-2-methyl-9-benzyloxy-4H-pyrido[1,2-a]-pyrimidine-4-one (HMBP, 5.03 g) in $POCl_3$ (2.45 ml) was heated to 91-95° C., under stirring, to afford a clear solution. The mixture converted to heavy paste at the end of the reaction. The mixture was heated to 60° C. and treated with a solution of methanol (10 ml) and toluene (25 ml) to afford the precipitation of the product. The cake was washed with toluene (3 ml) to afford 2.43 g of wet product, which was dried in air for 3 days to afford 1.69 g of the crystalline CMHP. Yield 46%.

Preparation of 3-(2-chloroethyl)-6,7,8,9-tetrahydro-9-hydroxy-2-methyl-4H-pyrrido[1,2-a]-pyrimidin-4-one (CMHTP)

Example 10

A mixture of CMBP (10.3 g, 0.031 mol) in methanol (100 ml) was treated with 32% HCl (4.3 g, 0.0376 mol) in an autoclave. The catalyst (10% Pd/C, 0.52 g) was added, the mixture was flushed twice with nitrogen, then hydrogen, finally filled with hydrogen to a pressure of 5 bar, heated to 65° C. and stirred over a 6 h period. The mixture was cooled to 20° C., the hydrogen was replaced with nitrogen and the mixture was filtered. The residue of the catalyst was washed with a little methanol. The filtrates were combined and evaporated under reduced pressure to afford 12.11 g of the product, as a crystallizing oil. The product was mixed with water (50 ml) and extracted with ethyl acetate (50 ml). The aqueous phase was neutralized with 10% $NaHCO_3$ solution (50 ml) and the organic products were extracted with DCM (5×25 ml). The extracts were washed with 10% $NaHCO_3$ (2×25 ml), followed by water (2×50 ml), dried overnight over anhydrous magnesium sulfate, filtered and evaporated, to afford 5.80 g of the crude CMHTP product.

Example 10A

Crystallization from ethyl acetate (25 ml) afforded 3.16 g of the title product. Additional amounts of the title product (total 1.35 g) were isolated from the filtrate by repeat crystallization from ethyl acetate to obtain CMHTP Form I having characterizing PXRD peaks at about 9.7, 19.4, 22.9 and 24.9+/−0.2 degrees 2θ and one or more additional PXRD peaks at about 22.0, 27.4, 28.1 and 39.4+/−0.2 degrees 2θ. The total yield of the CMHTP Form I product, in a purity of >93%, was 4.51 g (60%).

Optional Step:

Example 10B

A slurry of CMHTP Form I (20 g) in 100 ml water was stirred at room temperature for 10 minutes. The solid was vacuum filtrated and washed with water (3×60 ml), ethyl acetate (60 ml) and dried overnight in a vacuum oven at 55° C. The solid was analyzed by XRD to give CMHTP Form II (FIG. 2) characterized by PXRD diffraction peaks at about: 8.5, 11.2, 15.3, 23.8+/−0.2 two theta. Preferably, this form also includes one or more additional PXRD peaks of the following: 17.0, 22.6, 25.6 and 29.7+/−0.2 two theta.

Example 11

A suspension of 3-(2-chloroethyl)-2-methyl-9-benzyloxy-4H-pyrido[1,2-a]pyrimidine-4-one (CMBP, 5.00 g) in methanol (30 ml) was treated with 32% HCl (1.72 g) to afford clear solution with pH 2. The solution was charged into a glass autoclave. The catalyst (0.12 g) was added. The mixture was heated to 48° C. and hydrogenated under hydrogen pressure of 3 bar over a 7.5-h period, until the level of CMBP reduced to <0.1%.

The reaction mixture was filtered and the used catalyst was washed with methanol (5 ml). The mother liquor and the washing were combined and charged into glass autoclave. Fresh catalyst (0.253 g) was added. The mixture was heated to 55° C. and hydrogenated under hydrogen pressure of 3 bars over a 24-h period, until the level of CMHP reduced to 0.9%. The reaction mixture was filtered and the used catalyst was washed with methanol (5 ml). The mother liquor and the washing were combined to afford 17.05 g clear solution (pH 1). The solution was evaporated under reduced pressure to remove volatiles and the viscous residue was dissolved in water (5 ml, pH 1-1.5). The aqueous solution was treated with 10% $NaHCO3$ (13.2 g) to adjust pH 7-8. The aqueous solution was extracted twice with dichloromethane (2×25 ml) and discarded. Extracts were combined and evaporated to afford 2.8 g of the crude CMHTP product, as solidifying oil. Yield 70%, purity 90.5%.

Preparation of 9-hydroxy risperidone (Paliperidone)

Example 12

A mixture of CMHTP (4.393 g, 0.0168 mol), 6-fluoro-3-piperidino-1,2-benzisoxazol (FPBI, 4.695 g, 0.0203 mol), sodium carbonate (4.968 g, 0.0422 mol) and potassium iodide (0.288 g, 0.0017 mol) in DMF (50 ml) was heated for 8 h at 85° C. The mixture was poured into water (500 ml) and extracted with DCM (4×100 ml). The extracts were combined, washed with water (4×100 ml), dried with anhydrous magnesium sulfate, filtered and evaporated under reduced pressure to afford the crude title product. Crystallization from acetonitrile (100 ml) afforded 4.63 g of the title product, in a purity of >90%. Yield 58%.

TABLE 1

Hydrogenation of CMBP hydrochloride over various catalysts in MeOH at 2.5-3.0 bar

| Catalyst/type According to Johnson Matthey | CC[1] | T[2] | Time, h | Composition of reaction mixture before work-up[3] | | | | | Yield[4] |
|---|---|---|---|---|---|---|---|---|---|
| | | | | MDHP | MHTP | CMHTP | CMHP | CMBP | |
| 10% Pd/C/338 | 5.06 | 55 | 24 | 3.9 | 5.3 | 87.6 | 0.9 | ND | 70 |
| 10% Pd/C/87L | 6.22 | 57 | 14 | 2.7 | 4.7 | 87.3 | 4.6 | <0.1 | 67 |
| 10% Pd/C/490 | 10.0 | 70 | 5 | 0.4 | 9.8 | 84.2 | 4.6 | ND | 68 |
| 10% Pd/C/39 | 2.4 | 48 | 22 | ND[5] | ND | ND | 50.2 | 48.3 | — |
| 10% Pd/C/90 | 2.5 | 48 | 5 | ND | ND | ND | 23.0 | 70.7 | — |
| Ra-Ni[6] | 7.6 | 74 | 10 | ND | 16.2 | 18.9 | 24.0 | 33.4 | — |
| 5% Rh/C/592 | 1.2 | 70 | 4 | ND | ND | 2.0 | 17.6 | 58.7 | — |
| PtO | 5.0 | 45 | 8 | 10 | 13 | 39 | 23 | ND | — |
| 5% Pt/C/117 | 10.0 | 54 | 8 | ND | ND | 1.9 | 22.6 | 60.7 | — |

Notes.
[1]CC stands for the catalyst concentration regarding to the substrate, % w/w.
[2]T stands for bath temperature in ° C.
[3]HPLC area %.
[4]Yield of the crude product.
[5]ND represents not detected even though the level of the compound was analyzed.
[6]Free base was taken as HCl reacts with the catalyst
10% Pd/C, type 338 is the best catalyst.

Invention claimed:

1. Crystalline 3-(2-chloroethyl)-6,7,8,9-tetrahydro-9-hydroxy-2-methyl-4H-pyrrido [1,2-a]-pyrimidin-4-one (CMHTP), characterized by powder X-ray diffraction (PXRD) peaks at about 9.7, 19.4, 22.9 and 24.9 +/−0.2 degrees 2θ.

2. The crystalline CMHTP of claim 1, further characterized by one or more of the following PXRD peaks: about 22.0, 27.4, 28.1 and 39.4 +/−0.2 degrees 2θ.

3. The crystalline CMHTP of claim 2, wherein the PXRD pattern is substantially as depicted in FIG. 1.

4. Crystalline 3-(2-chloroethyl)-6,7,8,9-tetrahydro-9-hydroxy-2-methyl-4H-pyrrido [1,2-a]-pyrimidin-4-one (CMHTP), characterized by powder X-ray diffraction (PXRD) peaks at about 8.5, 11.2, 15.3, 23.8 +/−0.2 degrees 2θ.

5. The crystalline CMHTP of claim 4, further characterized by one or more of the following PXRD peaks: about 17.0, 22.6, 25.6 and 29.7 +/−0.2 degrees 2θ.

Figure 2:
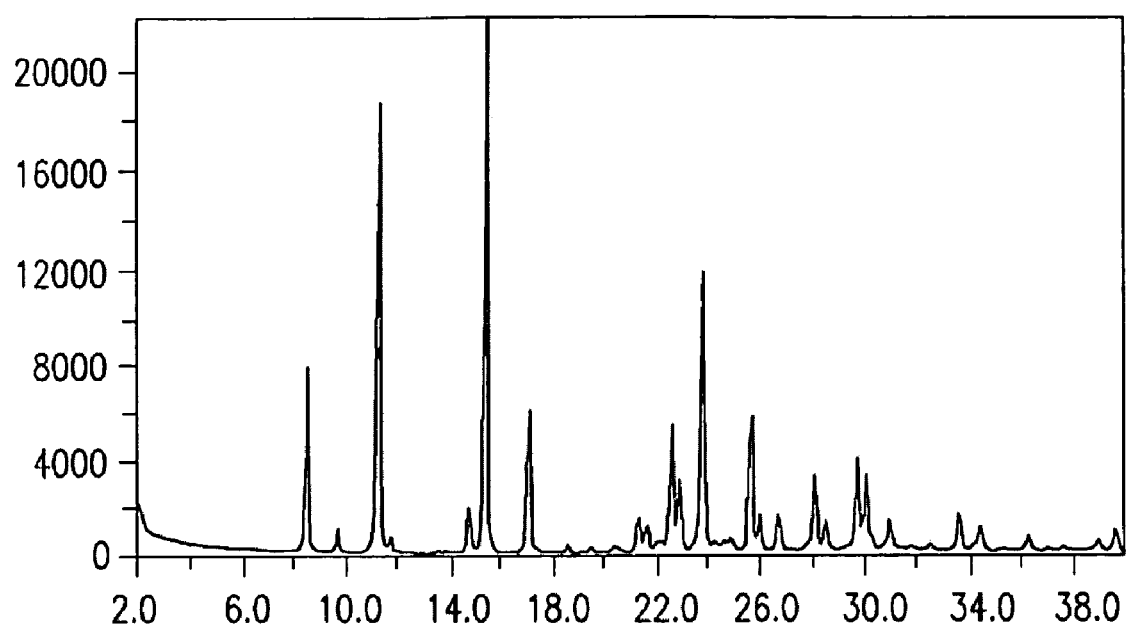
FIG. 2 illustrates a representative powder X-ray diffraction pattern for CMHTP Form II.

6. The crystalline CMHTP of claim 5, wherein the PXRD pattern is substantially as depicted in FIG. 2.

7. Solid 3-(2-chloroethyl)-6,7,8,9-tetrahydro-9-hydroxy-2-methyl-4H-pyrrido[1,2-a]-pyrimidin-4-one (CMHTP).

8. 3-(2-Chloroethyl)-2-methyl-9-hydoxy-4H-pyrido[1,2-a]pyrimidine-4-one (CMHP).

9. The CMHP of claim 8, wherein the CMHP is solid.

10. 3-(2-Hydroxyethyl)-2-methyl-9-benzyloxy-4H-pyrido[1,2-a]pyrimidine-4-one (HMBP).

11. The HMBP of claim 10, wherein the HMBP is amorphous solid, crystalline or substantially isolated.

12. A process for preparing crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 9.7, 19.4, 22.9 and 24.9 +/−0.2 degrees 2θ, comprising crystallizing CMHTP from ethyl acetate.

13. A process for preparing crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 8.5, 11.2, 15.3, 23.8 +/−0.2 degrees 2θ, comprising:
  stirring starting solid CMHTP in water to form the product CMHTP characterized by powder X-ray diffraction (PXRD) peaks at about 8.5, 11.2, 15.3, 23.8 +/−0.2 degrees 2θ, wherein the starting solid CMHTP is crystalline 3-(2-chloroethyl)-6,7,8,9-tetrahydro-9-hydroxy-2-methyl-4H-pyrrido[1,2-a]-pyrimidin-4-one (CMHTP), characterized by powder X-ray diffraction (PXRD) peaks at about 9.7, 19.4, 22.9 and 24.9 +/−0.2 degrees 2θ.

14. The process of claim 13, wherein the stirring is at about room temperature for a duration of about 5 minutes to about 60 minutes, and wherein room temperature is about 18° C. to about 25° C.

15. The process of claim 14, wherein the duration is about 10 minutes.

* * * * *